(12) United States Patent
Leibholz et al.

(10) Patent No.: US 6,478,856 B1
(45) Date of Patent: Nov. 12, 2002

(54) APPARATUS AND METHOD FOR COLLECTION, SORTING, CONCENTRATING AND IMPINGING PARTICLES ON A SURFACE

(76) Inventors: Stephen Leibholz, 1204 Pheasant Rd., Rydel, PA (US) 19046; Sir John Manniello, 9 Island Ave., Suite 801, Miami Beach, FL (US) 33109

( * ) Notice: Subject to any disclaimer, the term of this patent is extended or adjusted under 35 U.S.C. 154(b) by 0 days.

(21) Appl. No.: 09/579,425

(22) Filed: May 26, 2000

(51) Int. Cl.[7] .......................... B01D 50/00; B01D 45/04; G01N 1/20
(52) U.S. Cl. .............................. 95/268; 55/326; 55/434; 73/863.21; 73/863.22; 73/863.41
(58) Field of Search ..................... 95/267, 268; 55/320, 55/321, 325, 326, 434; 73/28.05, 28.06, 863.41, 863.21, 863.22, 202; 209/134, 139.1

(56) References Cited

U.S. PATENT DOCUMENTS 4,215,565 A * 8/1980 Zanker ........................ 374/112
4,481,833 A * 11/1984 Bajek .......................... 137/544

\* cited by examiner

*Primary Examiner*—Robert A. Hopkins
(74) *Attorney, Agent, or Firm*—Roberts Abokhair & Mardula, LLC

(57) ABSTRACT

The present invention is drawn to an apparatus and method for collection, sorting, concentrating and impinging particles on a surface, primarily for use in detecting and classifying chemicals, particles, vira, and bacteria in fluids. In addition to mechanical and aerodynamic filtering, the present invention uses isokinetic filtering to acquire particles of interest by creating a local vortex in the fluid through use of a dam element at a high angle of attack. This isokinetically sorts particles by density and aerodynamic diameter.

20 Claims, 7 Drawing Sheets

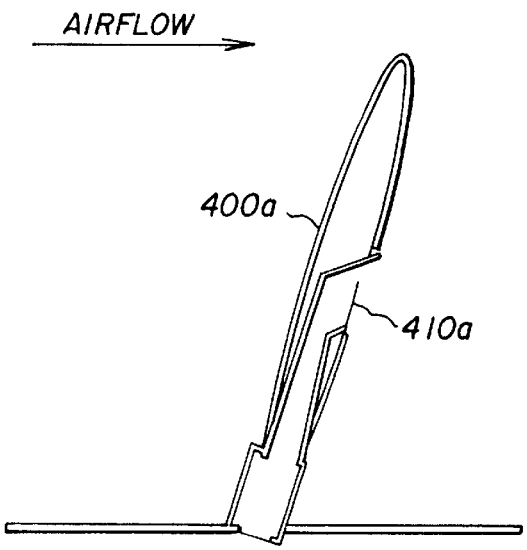
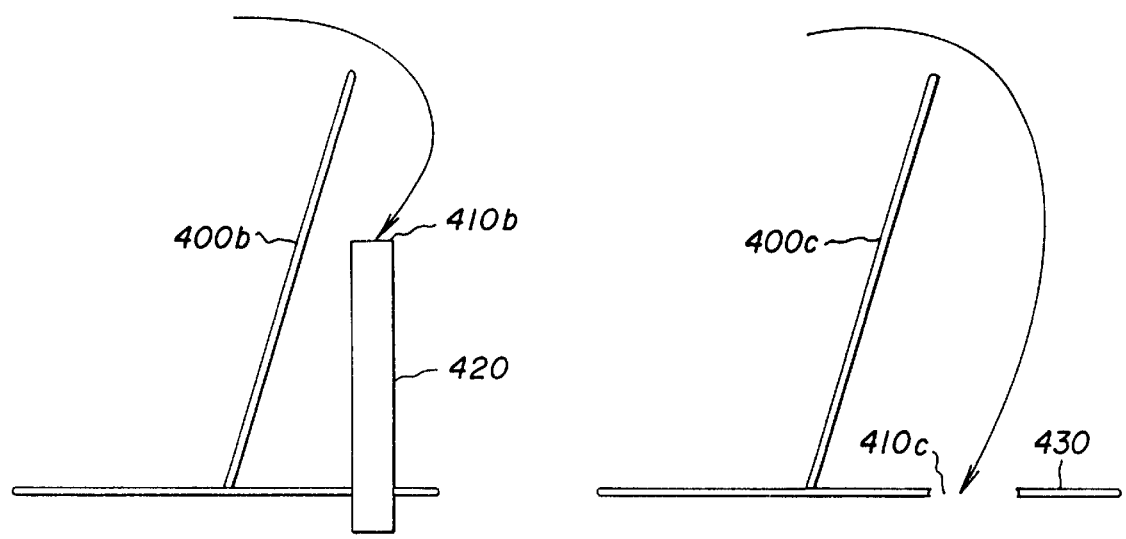
Fig. 4a
Fig. 4b
Fig. 4c

APPARATUS AND METHOD FOR COLLECTION, SORTING, CONCENTRATING AND IMPINGING PARTICLES ON A SURFACE

FIELD OF THE INVENTION

The present invention is drawn to an apparatus and method for collection, sorting, concentrating and impinging particles on a surface. More particularly, the invention is drawn to an impingement system for directing agents onto a detector surface for use in detecting and classifying chemicals, particles, vira, and bacteria in fluids.

BACKGROUND INFORMATION

Chemical and biological weapons, sometimes referred to as the "poor man's nuclear weapons," pose a significant threat in the post-Cold War environment. The relative low cost and simplicity of their design and technology, in comparison to nuclear weapons, make them the weapons of mass destruction choice for a variety of rogue states and terrorist, non-state organizations. This threat has been made all the more tangible by the use of chemical agent in a Tokyo subway, and allegations over Iraq's development of chemical and biological weapons and its actual use of chemical weapons in combat operations.

According to the 1998 U.S. Army Science and Technology Master Plan, "New fluorescent, acoustic, and optical biosensors are being designed for enhanced sensitivity and more flexible detection capability. Recent advances in the acceleration of the polymerase chain reaction (PCR) on a miniaturized scale now permit the exploitation of DNA probes for field detection of pathogens. A major thrust of a Joint Warfighting Science and Technology Plan (JWSTP) Defense Technology Objective (DTO), J.04 "Integrated Detection Advanced Technology Demonstration (ATD)," is the development of a rapid, automated field detection device based on the PCR. One key DTO element is the development of recombinant antibodies to serve as the recognition element of these new biosensors (FY98). Recombinant antibodies will ultimately be designed and quickly selected from genetic "super libraries" (FY99) to have specific detection capabilities, and novel starburst dendrimers are being studied for use on tailored reactive surfaces. Another major approach to point detection is mass spectrometry (MS), and miniature automated pyrolysis-based versions are being assessed for integration into existing CBD platforms (FY01). Of critical importance for biosensor and MS approaches is bio-aerosol sampling, since characteristics (e.g., concentration of detectable units per unit volume of air) of biological aerosols differ dramatically from chemical vapors, with resulting effects on detection efficacy."

BRIEF SUMMARY OF THE INVENTION

It is an object of the invention to provide a structure for sorting and selecting components of a fluid for acquisition and impingement on a sensor surfaces for alarm and/or analysis purposes.

It is another object of the invention to provide the functions of acquisition, filtering, sorting, selection, impingement and trapping of particles in a fluid, in accordance with desired mathematical functions of size, density, shape and surface characteristics.

It is another object of the invention to provide a combination of mechanical, aerodynamic, and kinetic methods to concentrate and/or sort particles of desired size and/or density from a fluid (gaseous, vapor or liquid).

It is another object of the invention to provide a combination of mechanical, aerodynamic, and kinetic methods to impinge particles of desired size and/or density onto a sensor surface.

It is yet another object of the invention to provide an impingement system for directing harmful agents onto a detector surface for use in detecting and classifying chemicals, particles, vira, and bacteria in fluids.

It is yet another object of the invention to provide diagnostic information and annunciation, either locally or remotely, within approximately 1 second or less of exposure to an agent in the free fluid, the time being short enough to become a function of the biochemical sensing apparatus alone, which is not part of this invention.

BRIEF DESCRIPTION OF THE DRAWINGS

FIGS. 4a–4c disclose isokinetic separators used in the present invention.

DETAILED DESCRIPTION OF THE INVENTION

The present invention is to method and apparatus for directing agents onto a detector surface for use in detecting and classifying chemicals, particles, vira, and bacteria in fluids. As used herein, the term fluid is intended to comprise, without limitation, any fluid including air and water.

Figure 1:
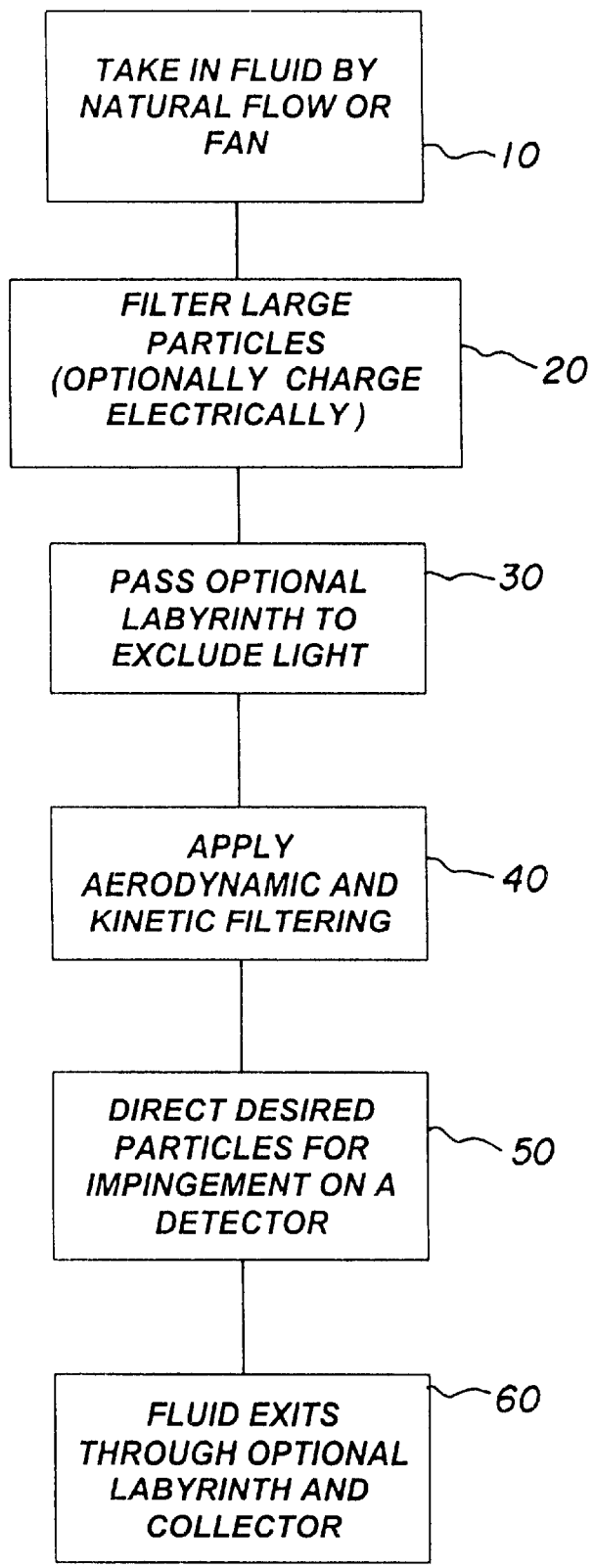
FIG. 1 discloses a basic schematic of the present invention.

In its most basic form, as shown in FIG. 1, the present invention provides a means to concentrate and impinge particles, spores, vapors, and gasses from air or another fluid medium. The fluid is taken in either through natural stream flows or via a small fan as shown at 10, and passed through a filter designed to remove large particles from the fluid as shown at 20. The resulting flow is then introduced into a chamber after optionally being electromagnetically charged and directed.

The impingement includes, without limitation, presenting pathogenic organisms, whether or not incorporated in aerosols, and/or toxins and poisons suspended in the fluid as aerosols, solutions, particles or by other means, onto sensitive surfaces of detectors, collectors, or other devices intended to process the material, as shown at 50.

The chamber consists of a series of collectors at one end, interspersed with one or more exit orifices. An optional sinusoidally or otherwise varying electrical field designed to optimally control the motion of the particles within the chamber sets up electrodynamic forces that cause the collectors, which are part of the electrodynamic apparatus, to attract the agents being collected and/or tested. This mechanism is discussed further below. The motion of the particles is generally in the form of a nonlinear vector motion and/or, but not limited to, a wave of increasing amplitude, terminating in impingement on the collector surface.

The remaining components of the fluid exit the chamber, and optionally pass through a finer filter to provide additional collection means.

The sensitive structure consists of a plate, volumetric receiver or array or other array of one or more sensitive detectors, each of which provides one or more components of the analysis that the entire system is assigned to accomplish (the specific sensitivities and contents of the sensitive detectors are not part of this document).

The fluid passage optionally contains a series of designed bends or labyrinth, as shown at 30 whose purpose is to block light from the sensitive materials, as well as providing a portion of the aerodynamic filtering. This is in addition to the conventional mechanical filtering cited above.

The aerodynamic and kinetic filtering of 40 consists of one or more of three components. First, the bends in the passage are designed to employ a balance of centrifugal and drag forces to select out particles whose ratio of radius-squared to total mass (i.e. density times radius-cubed times four-thirds Pi) meets desired characteristics, mediated by the deliberately variable airflow in the bent section. Other mathematical functions serving as criteria for forting and selection include Bernoulli forces, and the effects of Reynolds and Froude Numbers as examples.

A structure bearing an aerodynamic functional resemblance to the Turbinate bone of vertebrate animals (found elsewhere in Nature as well) is optionally utilized to assure proper randomization of the components, as well as to cause early non-sensitive impingement of particles of undesired effective (i.e. aerodynamic) diameters.

In the preferred embodiment the optimum particle size for impingement is matched to the alveolar capture function, described below.

Each sensitive detector is optionally covered with a small trapdoor which when closed by electrical or mechanical means seals an associated detector. When open, the trapdoor optionally erects to a critical angle obtuse to the fluid stream, providing further optional selection of components of the stream using laminar or turbulent vortices to further provide discrimination for particle size and density.

The optional electromagnetic component of the device consists of a varying electrostatic field with incidental magnetic field optimized to accelerate particles of the appropriate size (surface area) and density onto the sensitive surface. The field either utilizes the induced dipole component of the particles being sorted or selected, or makes use of an electrostatic monopole on the each of the particles, using traditional methods for inducing the electrostatic monopole.

The fluid exits from the chamber (i.e., the chamber containing the plate or array and associated components) through holes in the plate or array interspersed among the detectors. The fluid then optionally passes through another light-restricting labyrinth to the exit and optional collection filter as shown at 60.

In a preferred embodiment of the present invention, for combining with a sensor, the system has the responsibility of:

(1) extracting desired aerosol and solid particles from the air, (2) eliminating particles of inappropriate size (e.g., dust on one end and smoke on the other), (3) sorting these particles while preserving viability of carried organisms, and (4) concentrating and impinging the desired particles on the sensitive surface of the sensor.

The system can be broken down into four subsystems, not precisely corresponding to the above functions. It is optimized for acquisition of particles (aerosol or solid) forming particular mammalian threats, i.e. nominally $1-5\mu$ in mean diameter.

Figure 2:
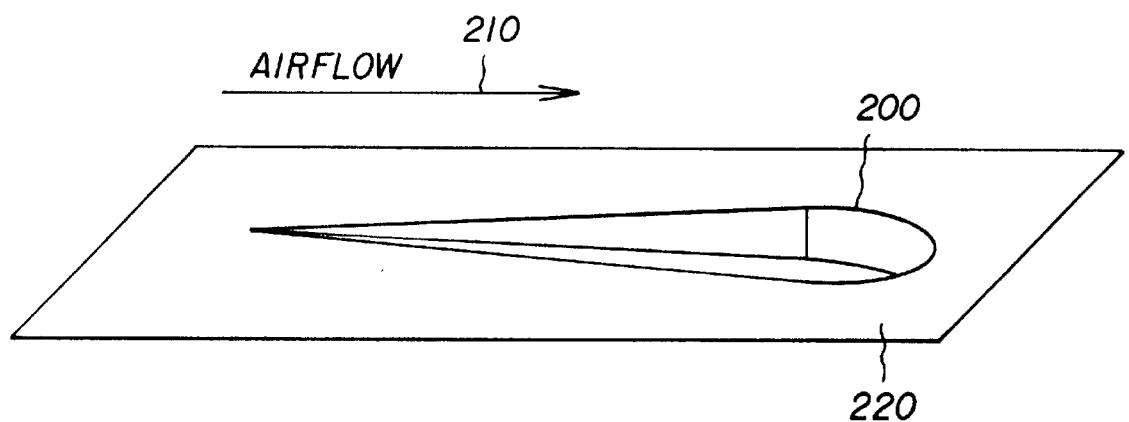
FIG. 2 discloses a preferred intake port for the present invention.

The first subsystem is concerned with particle acquisition and large-particle sorting. The challenge is that of capturing valid air samples despite wind direction and velocity. For this task the present invention preferably uses an omnidirectional assembly of the NACA flush intake design used in low-speed aircraft, which has the advantage of providing a positive Bernoulli-derived pressure to assure that sampling takes place. This has the further advantage of minimizing rain and small-particle effects, which could have an undesired effect on a sensor package. One such flush intake is diagrammed in FIG. 2 in which fluid such as airflow 210 is taken into NACA intake 200 in plate 220. One such duct is of course partially unidirectional.

Figure 3:
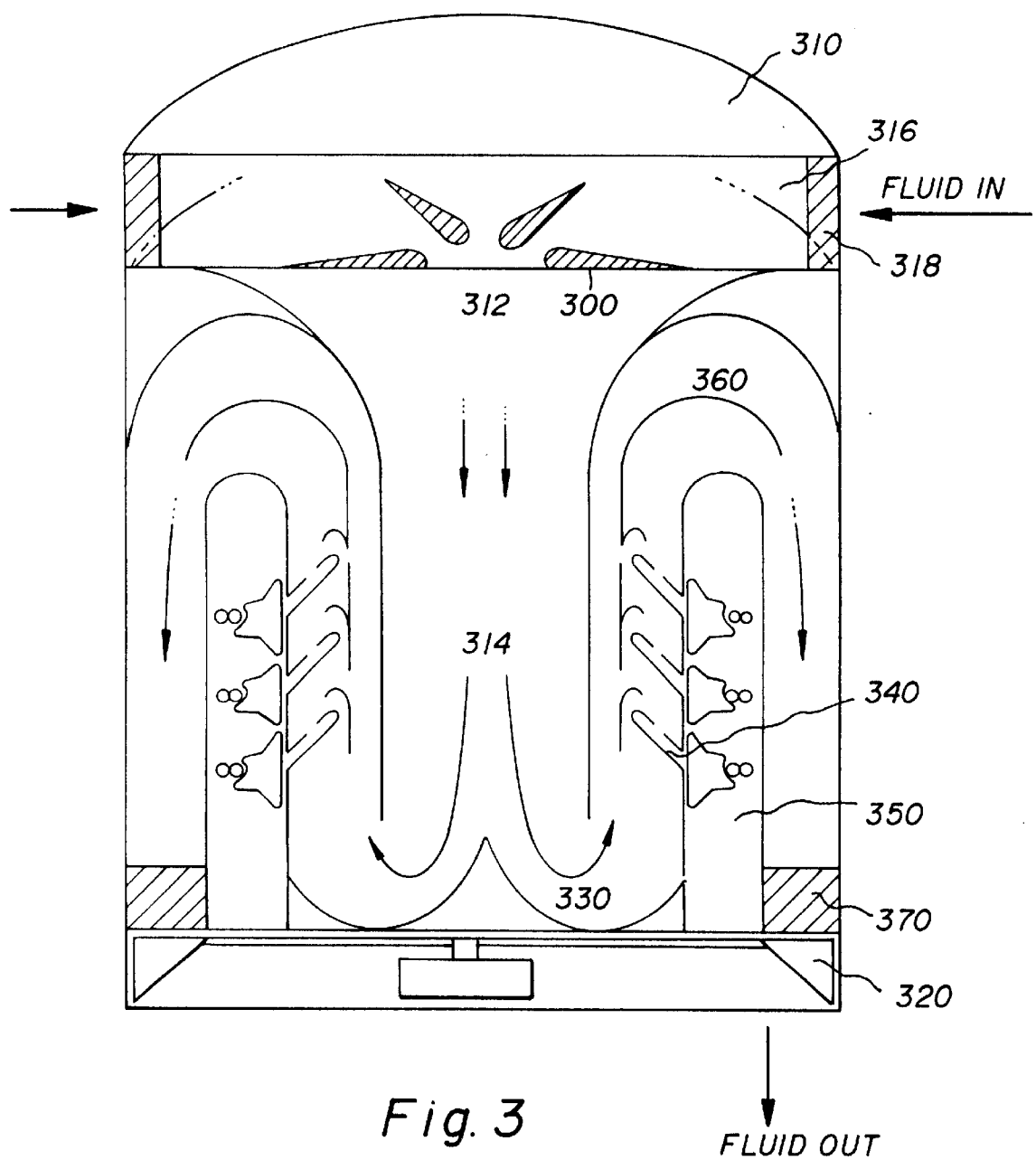
FIG. 3 discloses a preferred embodiment of the present invention.

To act omnidirectionally, the system can use four or more such intakes 300 disposed around a circle, and covered by a hat or cover 310, as shown in FIG. 3. These intakes 300 have a common (large-diameter) central opening 312, with a smooth transition to a common intake 314.

The main motive power for sampling is provided by a small DC-operated axial fan 320 moving approximately 15 L/m of air at very low pressure (pressure to be determined experimentally). This fan may be placed at the entrance or exit of the system.

The next subsystem concerns mechanical filtering. The entranceways 316 to these intakes 300 are covered by a mechanical dust filter 318 of high porosity. This filter 318 can be prepared using laser forming techniques and a hydrophobic base, available from Laserfare Inc. of Newport, RI. The design of the filter should be made to exclude particles of minimum diameter >10 $\mu$m with minimum back-pressure.

The mechanical filtering components generally act on the mechanical minimum diameter of a particle. In the region of interest here, the Reynolds Number Re<1 and the orientation of an elongated particle is random. However, the primary filtering method to eliminate, for example, dust and smoke, must therefore act on the aerodynamic (actually Stokes) diameter of the particle, and therefore mechanical filtering is insufficient.

Note that from elementary geometric considerations derived from close-packing theory, the maximum theoretical porosity of such a filter can be shown to approximate $$\frac{\pi}{2\sqrt{3}}.$$

Practical porosities of the order of 80% are therefore attainable, provided that a nonrandom filter-building process is utilized. A randomly generated filter (such as might be prepared chemically) has much lower porosity. The optimal design is that of a hexagonal lattice in the X and Y dimensions (normal to the airflow) and a slightly bent tube in the Z direction. At the time of manufacturing, the laser-cut filters can be used to prepare molds for casting multiple copies, to reduce costs.

Because mechanical filtering alone is insufficient for desired system, the next subsystem concerns aerodynamic isokinetic filtering. Selection of particles having the desired aerodynamic diameters (as opposed to minimum diameters) is aerodynamic in nature. FIGS. 4a–4c illustrate the general dam mechanism as element 400a, 400b, and 400c. In FIG. 3, the fluid passes labyrinth 330 to pass over dams 340 for isokinetic filtering to collect particles of interest for impingement on the sensors of sensor array packages 350, which are preferably replaceable. Remaining fluid passes exit labyrinth 360 to exit/collection filter 370 and fan 320.

The design of the isokinetic filter is somewhat counterintuitive, involving dams 400a, 400b, or 400c at angles of attack (α) in the deep-stall region, i.e., greater than 90° in the preferred embodiment, but is borne out by research, analysis and computer simulation. In the regime of interest, aerosol particles having approximately the same density can be sorted by mean aerodynamic diameter quite efficiently. For the regions of interest, the diagram of FIGS. 4a–4c are illustrative, and preliminary calculations have established the notional angle of attack of the aerodynamic filter.

In FIG. 4a, orifice 410a acquires particles of interest for impingement onto a surface. It is integrated into the dam 400a and is located on a backside (i.e., downstream side) thereof at a location appropriate for the desired isokinetic sorting. FIGS. 4b and 4c disclose similar embodiments. In FIG. 4b, a collection tube 420 is used to position an orifice 410b and in FIG. 4c, orifice 410c is positioned on the base 430 adjacent to the dam 400c.

The common aspect of all of these embodiments is that the orifice is at the downstream side of the dam. Locating the orifice on the dam, on a separate collection tube, or on the base adjacent to the dam, but on the downstream side thereof, facilitates the isokinetic sorting. The ratio of stream velocity to orifice velocity, the angle of the dam, and the position and size of the orifice regulate the distribution of particles that enter the orifice. This is demonstrated in the simulation.

Although orifices 410a and 410c will generally be fixed, orifice 410b can optionally be easily repositioned by making collection tube 420 movable. For example, although there is no functional difference between an orifice 410a in the dam 400a and an orifice 410b on a collection tube 420 positioned to be shielded by the dam 400b from the prevailing flow vector, the angle of collecting tube 420 with respect to the base (i.e., X-axis) is also a solution variable. Sorting can be varied based on repositioning of the collection tube 420. Dam 400c can also have utility as a trap door to cover a sensor.

Figure 7:
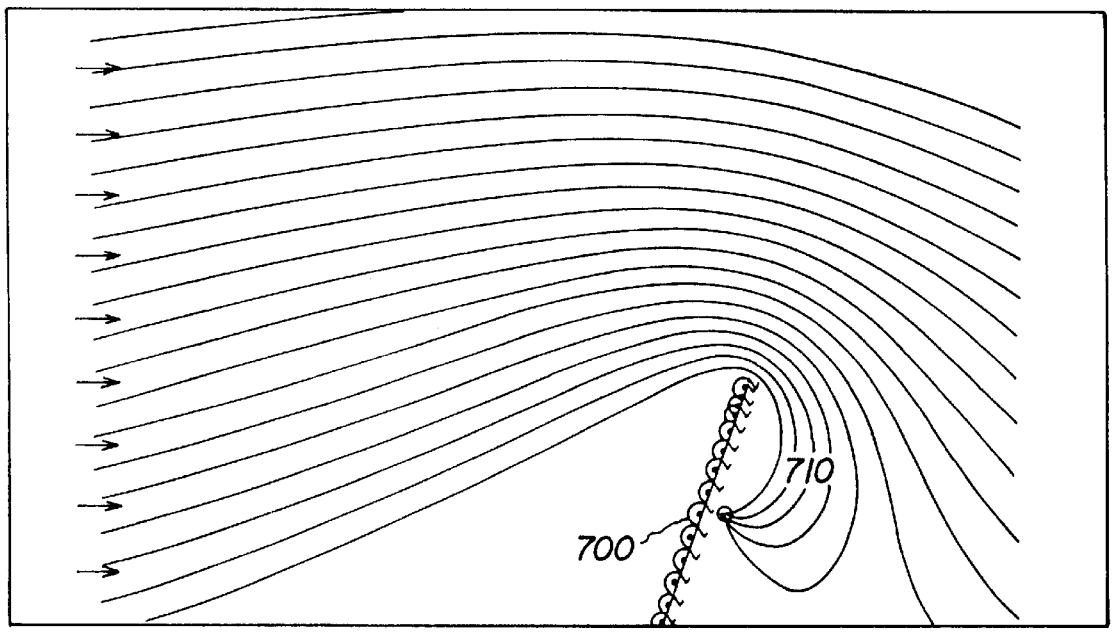
FIG. 7 discloses potential-based fluid flow mathematical simulation results for the aerodynamic sorting of the present invention.

Basically, as shown in FIG. 7, the dam 700 sets up a local vortex 710 which sorts the particles isokinetically, by density and aerodynamic diameter. The underlying theory is also discussed below, with preliminary analysis of the phenomenon, both extrapolated from experimental data and supported by a first-order simulation.

The final subsystem concerns impaction. After some analysis, the present inventors have concluded that the conventional aerodynamic impaction methodologies exhibited in commercial off-the-shelf viable-particle impactors are satisfactory and probably optimal for the present application. An existing impaction chamber design, such as those available from Anderson Instruments, 500 Technology Court, Smyrna, Ga. 30082, USA, is therefore usable for the present invention.

Figure 5:
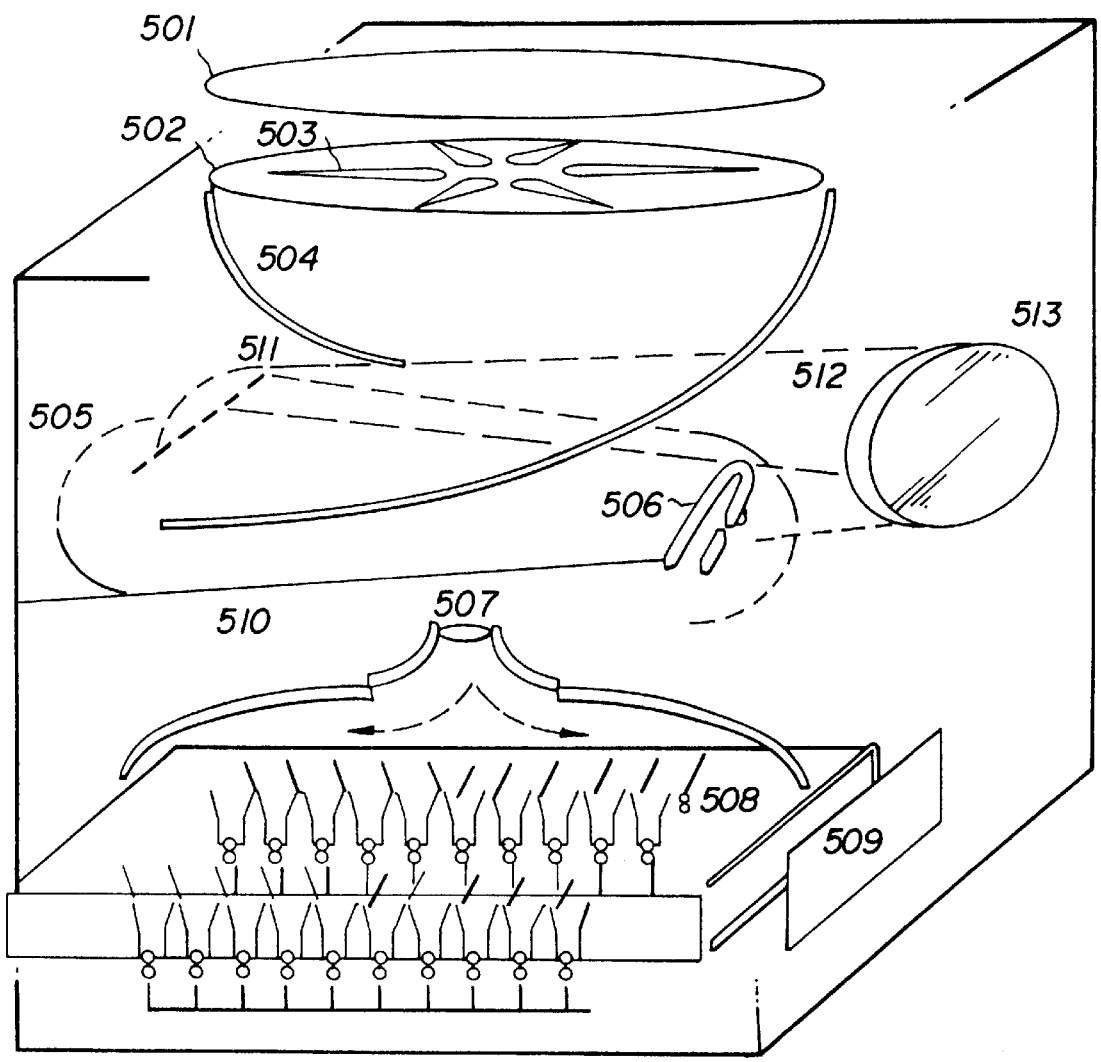
FIG. 5 discloses an alternative embodiment of the present invention.

FIG. 5 illustrates an alternate embodiment of the invention in which such an impaction chamber 507 is employed. In this embodiment, large particles and rain are excluded by input rain and sun hat 501 and large particle filter 502. Fluid then passes through NACA fluid dynamic intake orifices 503 to a collector and second filter 504 to an intake labyrinth and venturi 505 that directs the fluid over fluid dynamic dam 506 which acts as an inertial filter to obtain particles of interest at an orifice at the rear. Particles of interest are directed by inertial impactor 507 (which can optionally be replaced with the electrodynamic impaction discussed above) over the open trap doors of sensors 508 which are optionally replaceable via drawer 509. The remaining fluid is collected in chamber 510, passed through exit labyrinth 511 to fan 512 to exit collector and filter 513.

The apparent particle density of an aerosol is generally much smaller than the actual density, with coefficients of sphericity (ratio of surface area of an equivalent sphere to actual surface area (A/Ao). This means that for organic aerosols the apparent density is uniformly less than unity, and in the range where Stokes'Law does not apply experimentally very well. For the region of interest it amounts to a correction to Stokes'Law, and the inventors have chosen to use experimental data as guidance. Below, it is noted that preliminary simulation results using the assumptions underlying Stokes'Law are quantitatively consistent with the extrapolated experimental data. Robinson (see *Comm. Pure Applied Math*, 9,69) demonstrated that in these cases gravitational and inertial collection efficiencies are additive.

From the point of view of alveolar deposition (which is most critical from an infection viewpoint, and therefore defines both threat and measurement). The most recent data from Lippmann (see Lippmann, M. "Regional Deposition of Particles in the Human Respiratory Tract", in *Handbook of Physiology,* American Physiological Society, Bethesda, Md. 1977) suggests that for both oral and nasal alveolar deposition the optimum aerodynamic diameter is of the order of 1–5 µm, with tails of about 0.7–7 µm at the 15% efficiency level.

Without belaboring the derivation, from Stokes' Law and the assumptions of low Reynolds Number it can be shown that gravitational settling is fairly independent of wind velocity (including turbulence) and is given by $$\text{Re}^2 \varphi = \frac{8*[(4/3)\pi r^3]\gamma_a \gamma g}{\pi \eta^2}$$

where Re is the Reynolds Number, which by definition=$2r\gamma_a V/\eta$ yielding the velocity V, and where γ=density of the particle
γα=density of the air
g=gravitational acceleration
η=viscosity of the air There are better approximations based on empirical data, but for this analysis and design purposes they can be ignored unless it is required to accurately measure particle density and mean radius.

Figure 6:
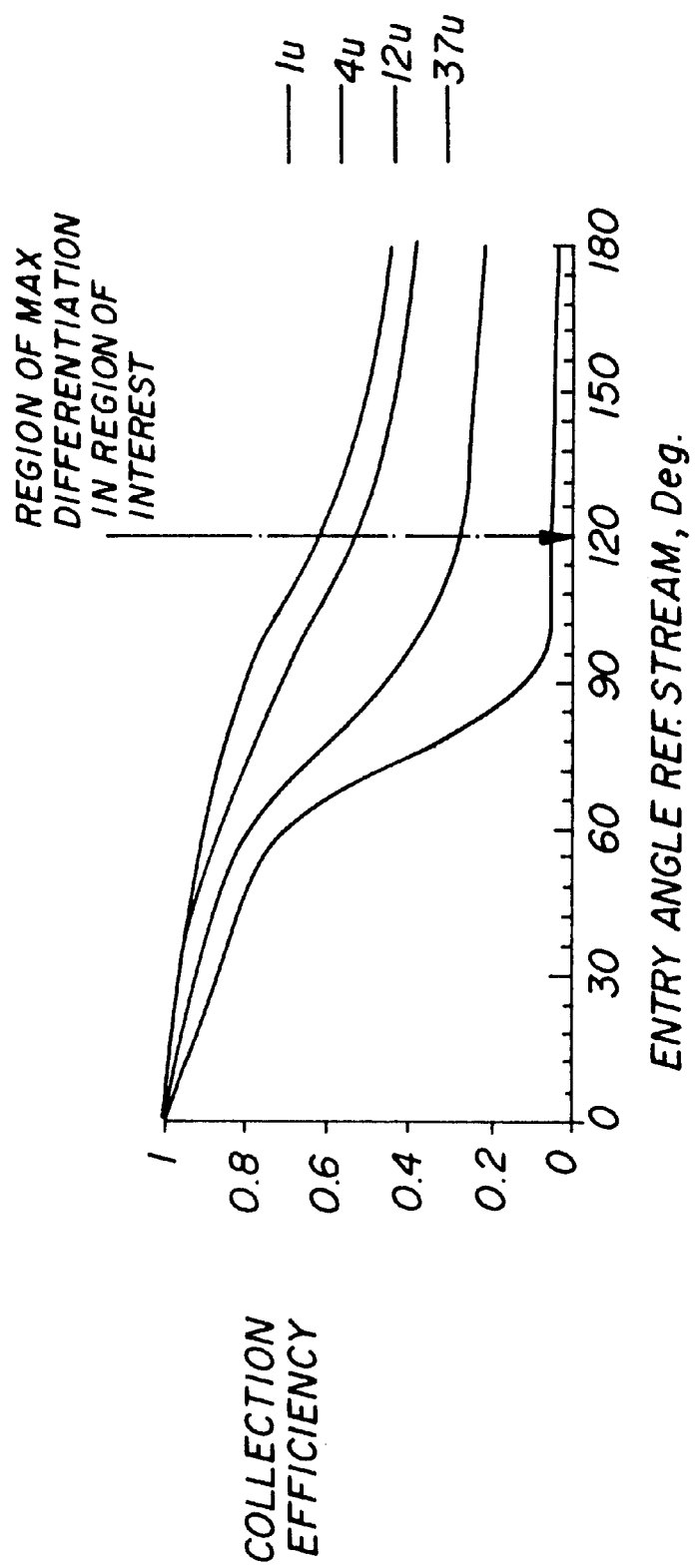
FIG. 6 discloses isokinetic flow model results for the present invention.

Data from Watson (see Amer. Ind. Hyg. Ass. Quarterly, 3,29) is shown in FIG. 6, which has been nondimensionlized (appropriate in the region of interest) has been extrapolated by the inventors to cover the expected particle size range ($\rho_{eff} \approx 1$), indicating how the sorting mechanism will select out particles of the appropriate size. These data are fortunately nondimensional, and confirm the present design and analysis. Most importantly, smoke particles, having effective diameters well under 0.5 µm will be rejected.

For the aerodynamic sorting, the entire air-handling problem is properly modeled by the Navier-Stokes formulation.

$$\left[\frac{\partial u_i}{\partial t}\right] + \left[\frac{\partial u_i}{\partial x_j}\right] \cdot [u] = -\frac{1}{\rho}\left[\frac{\partial p}{\partial x_j}\right] + \begin{bmatrix} 0 \\ 0 \\ -g \end{bmatrix} + \frac{\mu}{\rho}\left(\sum_j \left[\frac{\partial^2 u_i}{\partial x_j^2}\right] + \frac{1}{3}\left[\frac{\partial^2 u_j}{\partial x_i \partial x_j}\right]\right)$$

supplemented by the Equation of Continuity (incompressible flow in this case) and the thermodynamic relationship (generally adiabatic flow with $\gamma \approx 1.5$, but also neglectable in this instance).

Using a potential-based fluid flow simulator, available from the U. Mich. Department of Aerospace Engineering, a simple model of an appropriate obstruction to uniform flow was modeled at an appropriate angle. The results are illustrated in FIG. 7. Assumptions included incompressibility, and irrotational laminar flow. These assumptions are appropriate to the scenario including the prevailing Reynolds numbers (<<1). A number of runs were made, varying appropriate parameters (i.e., ratio of source to sink rates and angle of incidence), to demonstrate the aerodynamic filtering mechanism.

The airfoil angle of incidence in the pictured simulation was 210°. The nondimensional input flow rate of the pictured simulation run was 1 $sec^{-1}$, and the sink rate was located at a notional fluid sink of 2 $sec^{-1}$ at the ventral center of an arbitrarily thin "sand dollar". Other ratios of source to sink rate (1:1 to 1:3) provided similar results. The streamlines are shown. The equipotential lines are of course orthogonal to the streamlines, and reveal no surprises.

From these results, it is fairly obvious under the conditions in which Stokes'Law is valid (these being the case) that, to the first order, a particle of density $\rho$ with a mean radius of r embedded in a much lighter fluid ($\rho_f << \rho_p$) having a curved path with radius $r_a$ and a flow velocity of va will have a terminal velocity component $v_p$ normal to the fluid streamlines (neglecting gravity, which can be vectorially added later) of:

$$v_p = \frac{4\rho r^2 v_a^2}{18\mu r_a} = K\frac{\rho r^2 v_a^2}{r_a}$$

which provides square-law sorting by particle size. Varying the incidence angle of course changes the flow and the local curvature of the streamlines, and the present invention anticipates an incidence angle of $180<\alpha<270$ (see simulation graphic) for particle sorting, and, from the simulation, for the stated conditions, $\alpha \equiv 210$ degrees seems optimal to provide the greatest dispersion of particle paths. Thus there is an approximate agreement between the extrapolated empirical data and the simulation.

The exact dam and entry angles can vary from those disclosed herein. (Note that 120° in the empirical diagram corresponds geometrically to an incidence angle of 210°.) This computational experiment merely serves (1) to demonstrate qualitatively the measured filtering effects and (2) provide a basis for detailed analytical simulation in the course of the project to optimize the aerodynamic sorting phase of the preferred embodiment of the present invention.

We claim:

1. A method of collecting, sorting, concentrating and impinging particles on a surface, comprising:

capturing a fluid sample by drawing it through an intake;

mechanically and/or aerodynamically filtering out particles >10 $\mu$m;

using a dam to set up a local vortex to isokinetically sort particles by density and aerodynamic diameter; and selecting particles within a selected size-range for impaction on a surface.

2. The method of claim 1, wherein said selected size range is 0.7–7$\mu$m.

3. The method of claim 1, wherein said selected size range is 1–5$\mu$m.

4. The method of claim 1, wherein said dam has an angle of attack >90 degrees with respect to said fluid.

5. The method of claim 1, wherein said dam has an angle of attack between 180 and 270 degrees with respect to said fluid.

6. The method of claim 1, wherein said dam has an angle of attack of 210 degrees with respect to said fluid.

7. The method of claim 1, wherein said fluid is air.

8. An apparatus for collecting, sorting, concentrating and impinging particles on a surface, comprising:

a fluid intake;

a mechanical filter with an effective mesh size of 10 $\mu$m; and a fluid flow conduit having at least one dam means to set up a local vortex to isokinetically sort particles by density and aerodynamic diameter, wherein said dam means includes means for selecting particles within a selected size-range for impaction on a surface.

9. The apparatus of claim 8, wherein said fluid intake is an omnidirectional array of NACA flush intakes.

10. The apparatus of claim 8, wherein said mechanical filter includes a labyrinth element to exclude light.

11. The apparatus of claim 8 wherein said mechanical filter comprises an element formed by laser forming or laser-formed molding techniques.

12. The apparatus of claim 8, wherein said selected size range is 0.7–7 $\mu$m.

13. The apparatus of claim 8, wherein said selected size range is 1–5 $\mu$m.

14. The apparatus of claim 8, wherein said dam means has an angle of attack >90 degrees with respect to said fluid.

15. The apparatus of claim 8, wherein said dam means has an angle of attack between 180 and 270 degrees with respect to said fluid.

16. The apparatus of claim 8, wherein said dam means has an angle of attack of 210 degrees with respect to said fluid.

17. The apparatus of claim 8, further comprising a fan positioned to cause fluid flow through said fluid intake.

18. The apparatus of claim 8, wherein said dam means includes an upstream dam element and said means for selecting particles is an orifice on a downstream side of said dam element, wherein said orifice is located at a position selected from the group comprising a downstream side of said dam element, an end of a collection tube located downstream of said dam element, and a base adjacent a downstream side of said dam element.

19. The apparatus of claim 8, wherein said fluid is air.

20. The apparatus of claim 8, wherein said surface is a sensor surface.

* * * * *